United States Patent [19]

Arena

[11] 4,313,884

[45] Feb. 2, 1982

[54] USE OF METAL IONS IN PREPARATION OF ANHYDROPOLYOLS

[75] Inventor: Blaise J. Arena, Des Plaines, Ill.

[73] Assignee: UOP Inc., Des Plaines, Ill.

[21] Appl. No.: 113,882

[22] Filed: Jan. 21, 1980

[51] Int. Cl.$^3$ .................. C07D 309/06; C07D 307/12; C07D 305/04

[52] U.S. Cl. .......................... 260/345.9 R; 260/347.8; 260/333

[58] Field of Search ..................... 260/347.8, 345.9 R, 260/333

[56] References Cited

U.S. PATENT DOCUMENTS

| | | | |
|---|---|---|---|
| 1,757,468 | 5/1930 | Müller et al. | 260/347.8 |
| 2,572,566 | 10/1951 | Himel et al. | 260/347.8 |

FOREIGN PATENT DOCUMENTS 629021  10/1961  Canada ............................ 260/347.8

Primary Examiner—Nicky Chan
Attorney, Agent, or Firm—James R. Hoatson, Jr.; Raymond H. Nelson; William H. Page, II

[57] ABSTRACT

Anhydrohexitols may be prepared from hexitols by heating the hexitols in the presence of metal ions whose charge to ionic radius ratio is from about 2.0 to about 3.2 at a temperature from about 100 to about 300° C. A hexose, such as glucose, may be converted directly to anhydrohexitols, such as sorbitans, by hydrogenating the hexose in the presence of a suitable hydrogenation catalyst to which has been added an appropriate metal salt, such as nickel chloride.

10 Claims, No Drawings

USE OF METAL IONS IN PREPARATION OF ANHYDROPOLYOLS

BACKGROUND

Emulsifiers find widespread utility in many areas. Especially prevalent in the food industry are derivatives of hexitol anhydrides, or anhydrohexitols. For example, the fatty acid derivative of anhydrohexitols commonyl are used in formulations of confectionary fats and margarines.

Hexitols are hexanehexols, that is, n-hexanes each of whose carbon atoms bears a hydroxyl group. Similarly, pentitols are pentanepentols and tetritols are butanetetrols. Hexitols, pentitols, and tetritols are members of the class of polyols. Hexitols are commonly derived from hydrogenation of hexoses, during which the carbonyl group is reduced to a hydroxyl group. A particularly common hexitol is sorbitol whose frequent incidence among hexitols of commerce may be attributed, at least in part, to its being derived from glucose, an abundant and cheap raw material of widespread occurrence.

Sorbitol and other hexitols may be converted to anhydrohexitols with acid. For example, when hexitol is heated with two molar hydrochloric acid at 100° C. for 100 hours a nearly quantitative yield of anhydrohexitols is obtained. Barker, R., J. Org. Chem. 35 p. 461, 1970.

It is desirable to prepare anhydrohexitols by a process to obviate the need of removing large quantities of acid where their presence is objectionable, as e.g., in subsequent use of the product in foodstuffs. It is also highly desirable to have a process whereby a hexose may be converted to anhydrohexitols in a single step.

SUMMARY OF THE INVENTION

An object of this disclosure is to provide a method of preparing anhydrohexitols, anhydropentitols, and anhydrotetritols from hexitols, pentitols, and tetritols, respectively in the absence of added acid. One embodiment is a process comprising heating a hexitol in the presence of a metal ion whose charge to ionic radius ratio is from about 2.0 to about 3.2, and recovering the formed anhydrohexitol. A more specific embodiment comprises heating the hexitol with lanthanum ion at a temperature from about 150° to about 250° C. In a still more specific embodiment the hexitol is sorbitol and the metal ion is nickel in its divalent state.

Another object of this invention is to provide a process for preparing anhydrohexitols from a hexose. One embodiment comprises hydrogenating a hexose in the presence of a metal ion whose charge to ionic radius ratio from about 2.0 to about 3.2. Another such embodiment comprises hydrogenating the hexose with a nickel catalyst in the presence of about 0.05 mole ratio of nickel chloride at about 250° C.

DESCRIPTION OF THE INVENTION

This disclosure relates to a method of preparing dehydration products of polyols selected from the group consisting of hexitols, pentitols, and tetritols. In the present application hexitols are used as a representative of the aforementioned group merely for convenience in describing the invention, and it is to be understood that the invention herein relates to the entire group of polyols and is not restricted to hexitols. The term anhydropolyols means the dehydration products formed in this invention from the polyols specified above.

The anhydrohexitols of this application include the dehydration products of all hexitols, regardless of the nature of the hexitol. In particular, the dehydration products include monoanhydrohexitols and dianhydrohexitols. Representative formulae of such anhydrohexitols are,

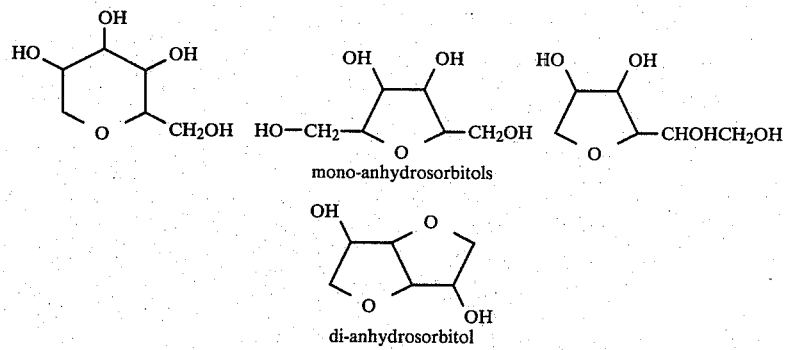

mono-anhydrosorbitols di-anhydrosorbitol

Sorbitol is a particularly pertinent hexitol because of its widespread availability; anhydrosorbitols commonly are referred to as sorbitans.

This invention relates to the discovery that certain metal ions cause dehydration of polyols, as for example hexitols to anhydrohexitols. In particular, it has been found that metal ions with a charge to ionic radius ratio from about 2.0 to about 3.2 effectively promote the formation of the desired products. By ionic radius is meant those values based on six-coordinated crystal structures as defined by L. Pauling, The Nature of the Chemical Bond, Cornell Univ. Press (1960). Among the metals whose ions satisfy the stated criteria are magnesium, calcium, titanium, manganese, iron, cobalt, nickel, copper, zinc, yttrium, actinium, thorium, protactinium, uranium, and the rare earth elements of the lanthanum series whose members are lanthanum, cerium, praseodymium, neodymium, promethium, samarium, europium, gadolinium, terbium, dysprosium, holmium, erbium, thulium, ytterbium, and lutetium. It has been found that those metallic ions whose charge to ionic radius ratio range from about 2.5 to about 3.2 are especially effective, hence are particularly desirable as metal ions to be used in this invention.

The nature of the cationic portion of the salt used to furnish the metal ion is not critical, so long as such cationic portion does not independently react with the polyol, such as hexitol, or hexose when used, and does not otherwise interfere with the desired reaction. Frequently it is convenient to use metal halides as the source of the metal ion, and the metal chlorides are especially desirable. The metal ion is employed in amounts from about 0.001 to about 0.1 mole ratio relative to polyol.

The reaction may be performed homogeneously, that is, in solution. When so performed, water commonly is used as the solvent. In this variation, a solution of hexitol from about 10 to about 50% or even more by weight of hexitol and a source of metal ion is heated in a suitable vessel. It has been found that a temperature from about 100° to about 300° C. will suffice, although a temperature from about 150° to about 250° C. is preferred. The reaction time will depend on the nature of the metal ion, the amount used, and the reaction temperature, but a time from about 1 to about 20 hours generally suffices. When the reaction is complete, the anhydrohexitol is recovered by suitable means. Where the reaction is more or less quantitative, a mixture containing chiefly anhydrohexitols may be obtained simply by removing water, as by distillation. Where the products are desired in a purer state, additional purification procedures may be necessary, as for example, fractional crystallization or chromatographic separation.

The dehydration of polyols, such as hexitols to anhydrohexitols, also may be conducted heterogeneously, particularly in the molten state. Thus, for example, a hexitol and a suitable metal salt may be mixed and thereafter heated to a temperature from about 100° to about 300° C. for a suitable time. Reaction conditions must be chosen to avoid charring or thermal degradation of reactants and products. In this variation it is necessary that the salt be adequately dispersed in the molten state.

The discovery of this invention may be advantageously incorporated in a process which directly converts a hexose to anhydrohexitols. Thus, a mixture of a hexose and a metal ion of the type previously described may be subjected to hydrogenation in the presence of a suitable catalyst. As the hexitol is formed, the metal ion effects dehydration to anhydrohexitols, thereby affording the product in a single step process.

For example, a solution of glucose containing nickel chloride may be hydrogenated at 500–1500 psig hydrogen in the presence of a commercial nickel hydrogenation catalyst at about 80°–250° C. The glucose initially is reduced to sorbitol, which then is directly dehydrated to sorbitan under the reaction condition. In this way it may be possible to effect conversion of glucose to sorbitan with yields of 85% or more in a simple one step process.

The examples cited herein are solely for purposes of illustration, and the invention is not to be construed as limited thereto.

EXAMPLE I

Reactions were conducted in a 250 ml stainless steel autoclave equipped with a 1500 RPM stirrer, heating mantle, and internal cooling coils. The feed consisted of 150 ml of a 33% by weight aqueous sorbitol solution containing a metal chloride at a mole ratio of 0.05. A commercial nickel hydrogenation catalyst was used at a concentration of 0.033 grams per ml solution. Hydrogen pressure was maintained at 700 psig and the reaction time was 5.5 hours at 225° C. When reaction was terminated, the mixture was analyzed by high pressure liquid chromatography, and components were further characterized by mass spectrometry, infra-red analysis, and nuclear magnetic resonance spectroscopy of acetylated derivatives. The results of such analyses are summarized in Table I.

TABLE I

| | Dehydration Of Sorbitol | | | | | | |
|---|---|---|---|---|---|---|---|
| | | | % Yields | | | | |
| | | 1,2-Propylene | Ethylene | | | Sorbitans | |
| Metal | Sorbitol | Glycol | Glycol | Glyerine | Mannitol | Mono-anhydro | Di-anhydro |
| $Ca^{++}$ | 46.9 | 7.6 | 4.0 | 2.4 | 2.9 | 24.9 | 4.1 |
| $Mg^{++}$ | 60.8 | — | 1.1 | 0.6 | 2.7 | 21.3 | 5.2 |
| $La^{+++}$ | 19.8 | 2.9 | 3.2 | 3.1 | 0.5 | 48.7 | 14.3 |
| $K^+$ | 54.5 | 10.0 | 3.2 | 3.6 | 6.4 | 5.6 | — |
| $Mn^{++}$ | 60.9 | 5.8 | 1.8 | 2.2 | 4.0 | 15.4 | 2.7 |
| $Ni^{++}$ | 5.0 | — | — | — | — | 59.5 | 27.5 |
| None | 71.2 | 5.7 | 9.2 | 5.5 | 2.6 | 2.2 | — |

As may be seen from the Table, some salts may have a profound effect on the yield of anhydrohexitols. Especially pronounced is the effect of nickel, which affords such anhydrohexitols in over 90% yield based on unrecovered sorbitol.

EXAMPLE II

Because it is known that anhydrohexitols are formed in the presence of acid, it was important to demonstrate that the effect of the added metal ions were unconnected with associated pH change. Accordingly, the pH of the sorbitol solution before and after addition of 0.05 mole ratio of various metal chlorides was measured, with results summarized in the following Table. These results show unequivocally that promotion of anhydrohexitol formation is a function of the metal ion, and not of any pH change induced by the presence of the metal salt.

TABLE II

| | Effect Of Added Salts On pH Of Sorbitol Solutions | |
|---|---|---|
| | pH | |
| Salt | before addition | after addition |
| $MgCl_2$ | 4.3 | 3.9 |
| $LaCl_3$ | 4.1 | 4.6 |
| $KCl$ | 4.1 | 4.3 |
| $MnCl_2$ | 4.4 | 8.0 |

EXAMPLE III

A mixture of anhydrous sorbitol (60.0 g) and nickel chloride hexahydrate (3.6 g) was heated with stirring at about 150° C. for about 4 hours, during which time water distilled from the mixture. The temperature then was raised to 215° C. while the pressure was lowered to about 5 mm Hg. About 26.5 g of a brown, viscous liquid was collected by distillation. Analysis by high pressure liquid chromatography indicated the material was comprised of about 70% anhydrohexitols.

EXAMPLE IV

A solution of 30% by weight erythritol (150 ml) containing nickel chloride hexahydrate at a mole ratio of 0.02 may be heated in a reaction vessel of the type described in Example I. After 8 hours at 260° C. the reacton may be terminated and the mixture analyzed for anhydrotetritols.

EXAMPLE V

A solution of 30% by weight xylitol (150 ml) containing nickel chloride hexahydrate at a mole ratio of 0.08 may be heated at 200° C. in a reaction vessel as described in Example I for about 6 hours. The anhydropentitols formed may be analyzed by suitable means, such as high pressure liquid chromatography.

What is claimed is:

1. A method of preparing anhydropolyols from polyols selected from the group consisting of hexitols, pentitols and tetritols which comprises contacting said polyol with a source of metal ions selected from the group consisting essentially of magnesium, manganese, iron, cobalt, nickel, copper, actinium, thorium, protactinium, uranium, cerium, praseodymium, neodymium, promethium, samarium, europium, gadolinium, terbium, dysprosium, holmium, erbium, thulium, ytterbium and lutetium at a temperature of from about 100° C. to about 300° C., and recoverying said anhydropolyols.

2. The method of claim 1 wherein the mole ratio of the metal ion to polyol is from about 0.001 to about 0.1.

3. The method of claim 1 wherein the temperature is from about 150° to about 250° C.

4. The method of claim 1 wherein said hexitol is sorbitol.

5. A method of preparing anhydrohexitols from a hexose comprising hydrogenating the hexose in the presence of metal ions whose charge to ionic radius ratio is from about 2.0 to about 3.2 at a temperature from about 80° to about 250° C., and recovering the anhydrohexitols formed thereby.

6. The method of claim 5 wherein the mole ratio of the metal ion to hexose is from about 0.001 to about 0.1.

7. The method of claim 5 wherein the metal ion is selected from ions of the group of metals consisting of magnesium, calcium, titanium, manganese, iron, cobalt, nickel, copper, zinc, and rare earth elements of the lanthanum series.

8. The method of claim 5 wherein the charge to ionic radius ratio is from about 2.5 to about 3.1.

9. The method of claim 5 wherein the temperature is from about 150° to about 250° C.

10. The method of claim 5 wherein said hexose is glucose.

* * * * *